US012636598B2

(12) United States Patent
Banju et al.

(10) Patent No.: US 12,636,598 B2
(45) Date of Patent: May 26, 2026

(54) FILTER HAVING A BASE AND A SUPPORT PORTION ON THE BASE

(71) Applicant: Murata Manufacturing Co., Ltd., Nagaokakyo (JP)

(72) Inventors: Masaru Banju, Nagaokakyo (JP); Shusuke Yokota, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 511 days.

(21) Appl. No.: 18/308,130

(22) Filed: Apr. 27, 2023

(65) Prior Publication Data

US 2023/0264120 A1     Aug. 24, 2023

Related U.S. Application Data

(63) Continuation of application No. PCT/JP2021/040957, filed on Nov. 8, 2021.

(30) Foreign Application Priority Data

Nov. 24, 2020     (JP) ................................. 2020-194522

(51) Int. Cl.
  B01D 29/05     (2006.01)
  B01D 39/20     (2006.01)
  C12N 1/02     (2006.01)
(52) U.S. Cl.
  CPC ......... B01D 29/05 (2013.01); B01D 39/2027 (2013.01); C12N 1/02 (2013.01); B01D 2201/0415 (2013.01)

(58) Field of Classification Search
  None
  See application file for complete search history.

(56) References Cited

U.S. PATENT DOCUMENTS 4,404,006 A *  9/1983  Williams ............... B01D 46/10
                                                      55/497
2016/0136552 A1   5/2016  Nakanishi et al.
                  (Continued)

FOREIGN PATENT DOCUMENTS

EP          1967265 A1    9/2008
JP          S58-045715 A   3/1983
                  (Continued)

OTHER PUBLICATIONS

International Search Report in PCT/JP2021/040957, mailed Jan. 18, 2022, 3 pages.

*Primary Examiner* — Hayden Brewster
(74) *Attorney, Agent, or Firm* — ArentFox Schiff LLP

(57)                ABSTRACT
A filter that includes: a filter base portion having a first main surface and a second main surface opposite to the first main surface, the filter base defining a plurality of through-holes communicating between the first main surface and the second main surface; and a support portion on the filter base portion, wherein the support portion includes: a main body portion on the first main surface and including a plurality of fixing portions in some of the plurality of through-holes; and a protruding portion protruding toward an outer side portion of the main body portion in a direction along the first main surface from a fixing portion located on a sidewall side of the main body portion among the plurality of fixing portions, and a thickness of the protruding portion is smaller than a thickness of the main body portion.

13 Claims, 12 Drawing Sheets

(56) References Cited

U.S. PATENT DOCUMENTS

| | | | |
|---|---|---|---|
| 2017/0121667 A1 | 5/2017 | Kikuhara et al. | |
| 2018/0312803 A1 | 11/2018 | Banju et al. | |
| 2019/0017012 A1 | 1/2019 | Banju et al. | |
| 2019/0225930 A1 | 7/2019 | Chen et al. | |
| 2021/0146309 A1 | 5/2021 | Banju et al. | |

FOREIGN PATENT DOCUMENTS

| | | | | |
|---|---|---|---|---|
| JP | 2017169551 A | 9/2017 | | |
| JP | 2018183100 A | 11/2018 | | |
| JP | 2019181352 A | 10/2019 | | |
| WO | 2015012315 A1 | 1/2015 | | |
| WO | 2015147086 A1 | 10/2015 | | |
| WO | 2018052847 A1 | 3/2018 | | |
| WO | WO-2018191611 A1 * | 10/2018 | ............. | B01D 29/48 |
| WO | 2020066578 A1 | 4/2020 | | |

* cited by examiner

FILTER HAVING A BASE AND A SUPPORT PORTION ON THE BASE

CROSS REFERENCE TO RELATED APPLICATIONS

The present application is a continuation of International application No. PCT/JP2021/040957, filed Nov. 8, 2021, which claims priority to Japanese Patent Application No. 2020-194522, filed Nov. 24, 2020, the entire contents of each of which are incorporated herein by reference.

FIELD OF THE INVENTION

The present invention relates to a filter.

BACKGROUND OF THE INVENTION

Patent Document 1 discloses a mesh member including a mesh having hollows for capturing particles and holes formed in the hollows, and an outer frame for fixing the outer periphery of the mesh. In the mesh member of Patent Document 1, a belt-like support frame embedded over a hollow and a hole continuous with the hollow is provided across opposing frame sides of the outer frame.

Patent Document 1: Japanese Unexamined Patent Application Publication No. 2019-181352

SUMMARY OF THE INVENTION

However, there is still room for improvement in the mesh member of Patent Document 1 in terms of prevention of clogging.

An object of the present invention is to provide a filter capable of preventing clogging.

A filter of one aspect of the present invention includes: a filter base portion having a first main surface and a second main surface opposite to the first main surface, the filter base portion defining a plurality of through-holes communicating between the first main surface and the second main surface; and a support portion on the filter base portion, wherein the support portion includes: a main body portion on the first main surface and including a plurality of fixing portions in some of the plurality of through-holes; and a protruding portion protruding toward an outer side portion of the main body portion in a direction along the first main surface, from a fixing portion located on a sidewall side of the main body portion among the plurality of fixing portions, and a thickness of the protruding portion is smaller than a thickness of the main body portion.

According to the present invention, it is possible to provide a filter capable of preventing clogging.

DETAILED DESCRIPTION OF THE PREFERRED EMBODIMENTS

Background of the Present Invention

Figure 1:
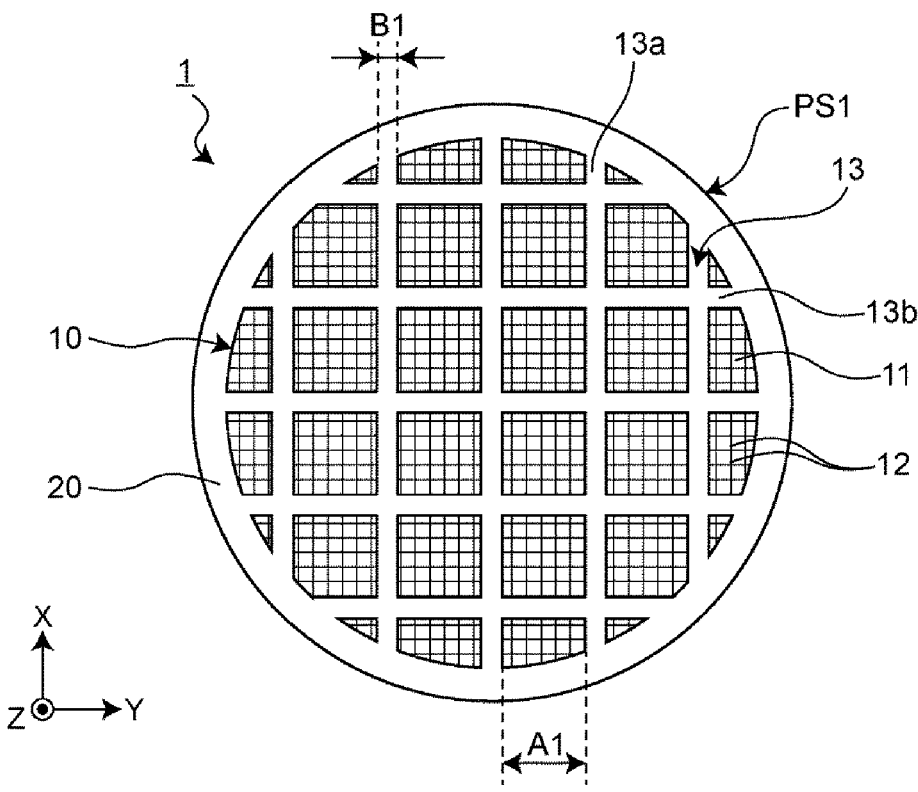
FIG. 1 is a schematic view of an example of a filter of Embodiment 1 according to the present invention as viewed from a first main surface side.

As in the mesh member described in Patent Document 1, a filter has been known in which strength is improved by providing a support portion in a filter base portion in which a plurality of through-holes is formed.

However, a filter provided with such a support portion still has room for improvement in terms of prevention of clogging. For example, there is an incomplete through-hole that is partially blocked by the support portion in the vicinity of the support portion. In this specification, "incomplete" means having a dimension smaller than a designed dimension in consideration of a manufacturing error. When a filtration object enters such an incomplete through-hole and clogging occurs, it becomes difficult to recover the filtration object. In addition, when the filtration object is a cell, the cell causing clogging dries and dies on the filter base portion, and it is difficult to recover the surviving cell.

In order to solve the above problems, the present inventors have found a filter provided with a support portion composed of a main body portion and a protruding portion arranged in the through-hole, and have completed the present invention. As a result, it is possible to prevent clogging due to the filtration object in the through-hole in the vicinity of the support portion. In addition, a liquid pool is formed in the vicinity of the support portion to suppress drying of the filtration object, and when the filtration object is a cell, death of the filtration object can be prevented.

A filter of one aspect of the present invention includes: a filter base portion having a first main surface and a second main surface opposite to the first main surface, the filter base portion defining a plurality of through-holes communicating between the first main surface and the second main surface; and a support portion on the filter base portion, wherein the support portion includes: a main body portion on the first main surface and including a plurality of fixing portions in some of the plurality of through-holes; and a protruding portion protruding toward an outer side portion of the main body portion in a direction along the first main surface, from a fixing portion located on a sidewall side of the main body portion among the plurality of fixing portions, and a thickness of the protruding portion is smaller than a thickness of the main body portion.

With such a configuration, it is possible to reduce the opening area of the incomplete through-hole and to prevent clogging of the filter due to a filtration object.

In the filter of a second aspect of the present disclosure, the filter base portion may have an inner wall extending from the second main surface toward the first main surface and which defines the plurality of through-holes, and the protruding portion may be in contact with the inner wall of the through-hole of the plurality of through-holes in which the fixing portion located on the sidewall side of the main body portion is arranged.

With such a configuration, it is possible to further prevent clogging of the filter due to the filtration object.

In the filter of a third aspect of the present disclosure, the protruding portion may have a surface continuous with the first main surface.

With such a configuration, it is possible to prevent the filtration object from entering the through-hole in the vicinity of the support portion.

In the filter of a fourth aspect of the present disclosure, the protruding portion may have a shape protruding from the first main surface.

With such a configuration, it is possible to prevent the filtration object from entering the through-hole in the vicinity of the support portion, and further to promote the movement of the substance requested to be separated from the filtration object to another through-hole.

In the filter of a fifth aspect of the present disclosure, a thickness of the protruding portion at a position in contact with the main body portion may be larger than a thickness of the protruding portion at a position in contact with the inner wall.

With such a configuration, it is possible to further promote the movement of the substance requested to be separated from the filtration object to the through-hole.

In the filter of a sixth aspect of the present disclosure, the protruding portion may have a shape recessed with respect to the first main surface.

With such a configuration, it is possible to form a liquid pool in the vicinity of the support portion and to suppress drying of the filtration object such as cells.

In the filter of a seventh aspect of the present disclosure, the protruding portion may seal a through-hole of the plurality of through-holes in which the fixing portion located on the sidewall side of the main body portion is arranged.

With such a configuration, it is possible to further prevent clogging of the filter due to the filtration object.

In the filter of an eighth aspect of the present disclosure, the sidewall is a first sidewall, the protruding portion is a first protruding portion, and the fixing portion is a first fixing portion, the main body portion may further include a second sidewall facing the first side wall, and the support portion may further include a second protruding portion protruding toward an outer side portion of the main body portion in a direction along the first main surface from a second fixing portion located on the second sidewall side of the main body portion among the plurality of fixing portions.

With such a configuration, it is possible to further prevent clogging of the filter due to the filtration object.

In the filter of a ninth aspect of the present disclosure, the support portion may include: a plurality of first support members having the main body portion and the protruding portion and extending in a first direction and a plurality of second support members having the main body portion and the protruding portion and extending in a second direction intersecting the first direction.

With such a configuration, strength of the filter can be improved.

Hereinafter, Embodiment 1 according to the present invention will be described with reference to the accompanying drawings. In addition, in each of the drawings, each element is illustrated in an exaggerated manner for ease of explanation.

Embodiment 1

[Overall Configuration]

Figure 2:
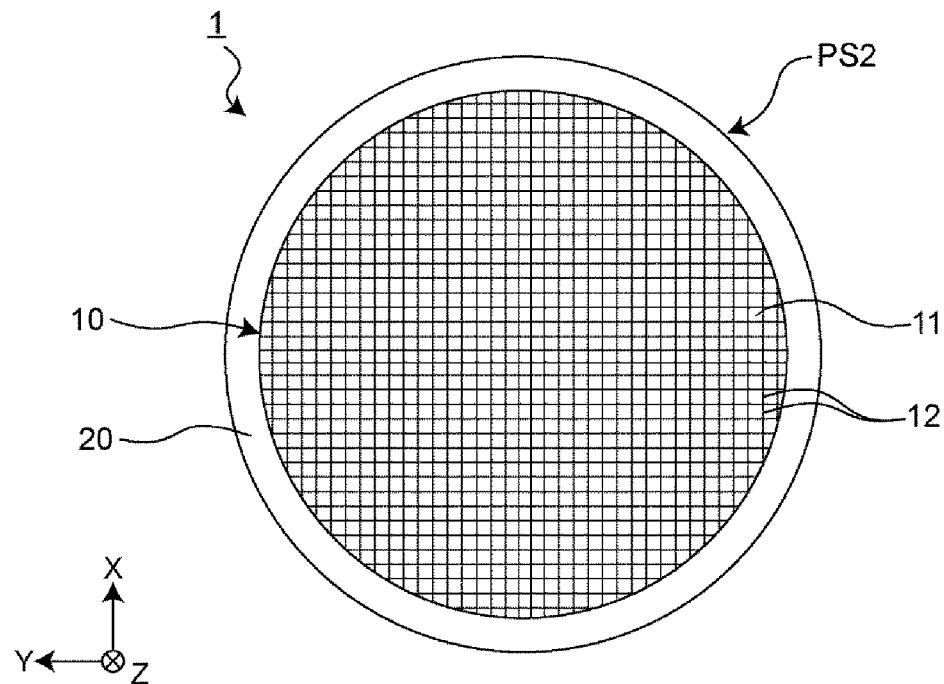
FIG. 2 is a schematic view of an example of the filter of Embodiment 1 according to the present invention as viewed from a second main surface side.

FIG. 1 is a schematic view of an example of a filter 1 of Embodiment 1 according to the present invention as viewed from a first main surface PS1 side. FIG. 2 is a schematic view of an example of the filter 1 of Embodiment 1 according to the present invention as viewed from a second main surface PS2 side. In the drawings, X, Y, and Z directions indicate a longitudinal direction, a lateral direction, and a thickness direction of the filter 1, respectively.

For example, the filter 1 is a filter that filters a fluid containing a filtration object.

In this specification, the "filtration object" means an object to be filtered of objects contained in the fluid. For example, the filtration object may be a biological substance contained in the fluid. The "biological substance" means a substance derived from an organism such as a cell (eukaryote), a bacterium (eubacterium), a virus or the like. Examples of cells (eukaryotes) include induced pluripotent stem cells (iPS cells), ES cells, stem cells, mesenchymal stem cells, mononuclear cells, single cells, cell aggregates, floating cells, adherent cells, nerve cells, leukocytes, cells for regenerative medicine, autologous cells, cancer cells, circulating tumor cells (CTCs) in the blood, HL-60, HELA, and fungi. Examples of bacteria (eubacteria) include Escherichia coli and Mycobacterium tuberculosis.

Examples of the fluid include a liquid and a gas. Examples of the liquid include a cell suspension.

The filter 1 is a metal filter. A material constituting the filter 1 contains at least one of a metal and a metal oxide as a main component. The material constituting the filter 1 may be, for example, gold, silver, copper, platinum, nickel, palladium, titanium, an alloy thereof, or an oxide thereof. In particular, by using titanium or a nickel-palladium alloy, the elution of metal is small, and the influence on the filtration object can be reduced.

As illustrated in FIG. 1 and FIG. 2, the filter 1 includes a filter portion 10 and a frame portion 20 provided on an outer periphery of the filter portion 10. In addition, the filter 1 has the first main surface PS1 and the second main surface PS2 opposite to the first main surface PS1. In Embodiment 1, the filter portion 10 and the frame portion 20 are integrally formed.

<Filter Portion>

The filter portion 10 is a portion that filters a fluid containing the filtration object. The filter portion 10 is composed of a filter base portion 12 in which a plurality of through-holes 11 communicating between the first main surface PS1 and the second main surface PS2 are formed. In addition, in the filter portion 10, a plurality of support portions 13 are arranged on the first main surface PS1 of the filter base portion 12.

The shape of the filter portion 10 is, for example, a circle, a polygon, or an ellipse when viewed from the thickness direction (Z direction) of the filter 1. In Embodiment 1, the shape of the filter portion 10 is a substantially circle. Note that in this specification, the term "substantially circle" means that the ratio of the length of the major diameter to the length of the minor diameter is equal to or more than 1.0 and equal to or less than 1.2.

<Frame Portion>

The frame portion 20 is a portion provided on the outer periphery of the filter portion 10, and having a smaller number of through-holes 11 per unit area than the filter portion 10. The number of through-holes 11 in the frame portion 20 is equal to or less than 1% of the number of through-holes 11 in the filter portion 10. The thickness of the frame portion 20 may be thicker than the thickness of the filter portion 10. With such a configuration, mechanical strength of the filter 1 can be increased.

When the filter 1 is used by being connected to an apparatus, the frame portion 20 may function as a connection portion that connects the filter 1 and the apparatus. Further, information of the filter 1 (dimension of the through-hole 11 and the like) may be displayed on the frame portion 20.

The frame portion 20 is formed in a ring shape when viewed from the first main surface PS1 side of the filter portion 10. When the filter 1 is viewed from the first main surface PS1 side, the center of the frame portion 20 coincides with the center of the filter portion 10. That is, the frame portion 20 is formed concentrically with the filter 1.

Hereinafter, the filter portion 10 will be described in detail.

Figure 3A:
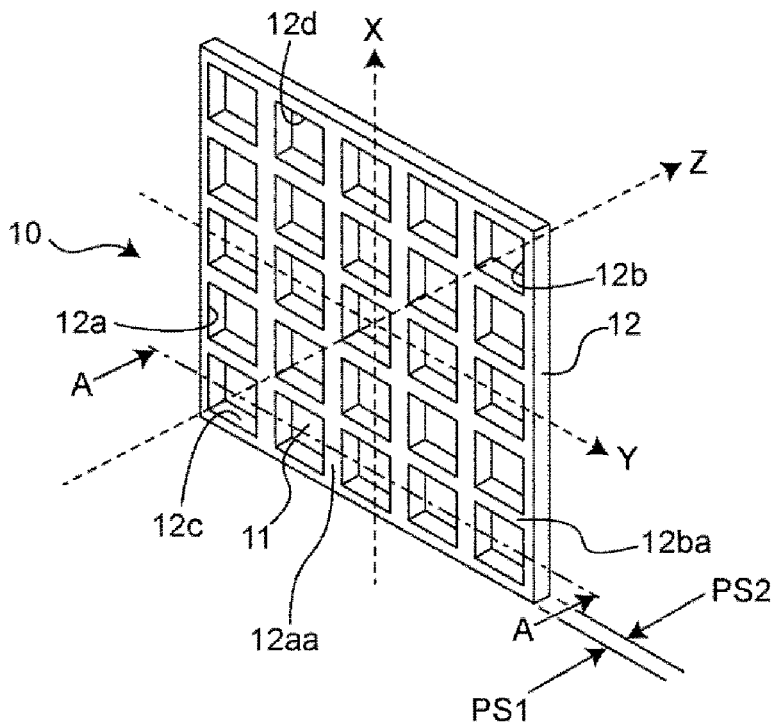
FIG. 3A is an enlarged perspective view of a part of a filter base portion.
Figure 3B:
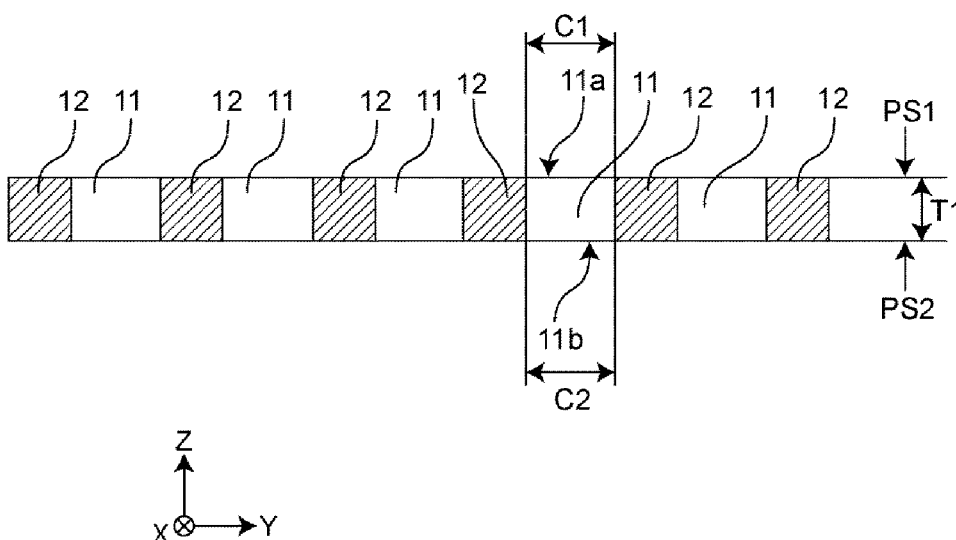
FIG. 3B is a cross-sectional view taken along a line A-A of FIG. 3A.

FIG. 3A is an enlarged perspective view of a part of the filter portion 10. FIG. 3A illustrates a part of the filter base portion 12 in which the plurality of through-holes 11 is formed in an enlarged manner. FIG. 3B is a cross-sectional view of the filter base portion 12 taken along a line A-A in FIG. 3A.

As illustrated in FIG. 3A, the plurality of through-holes 11 is periodically arranged on the first main surface PS1 and the second main surface PS2 of the filter portion 10. Specifically, the plurality of through-holes 11 is provided at equal intervals in a matrix in the filter portion 10.

In Embodiment 1, the plurality of through-holes 11 is provided along two arrangement directions orthogonal to each other, that is, along the X direction and the Y direction in FIG. 3A when viewed from the first main surface PS1 side (Z direction) of the filter portion 10. Note that the plurality of through-holes 11 may be provided in the filter portion 10, and the arrangement direction is not limited.

As illustrated in FIG. 3A, the filter base portion 12 in which the through-hole 11 is not formed is formed in a lattice shape. To be specific, in the filter portion 10, the filter base portion 12 includes a plurality of first base members 12aa arranged at equal intervals and extending in a first direction (X direction) and a plurality of second base members 12ba arranged at equal intervals and extending in a second direction (Y direction) intersecting the first direction (X direction).

The plurality of first base members 12aa and the plurality of second base members 12ba are formed of plate-shaped members. The plurality of through-holes 11 is defined by the intersection of the plurality of first base members 12aa and the plurality of second base members 12ba. In Embodiment 1, the first direction in which the plurality of first base members 12aa extends is the X direction, and the second direction in which the plurality of second base members 12ba extends is the Y direction. That is, in Embodiment 1, the first direction and the second direction are orthogonal to each other.

In Embodiment 1, the plurality of first base members 12aa and the plurality of second base members 12ba are integrally formed.

The filter base portion 12 has a first inner wall 12a, a second inner wall 12b, a third inner wall 12c, and a fourth inner wall 12d extending from the second main surface PS2 toward the first main surface PS1 and defining the plurality of through-holes 11. In Embodiment 1, the first inner wall 12a, the second inner wall 12b, the third inner wall 12c, and the fourth inner wall 12d each are formed by a flat surface extending from the second main surface PS2 toward the first main surface PS1 of the filter base portion 12. As illustrated in FIG. 3A, the first inner wall 12a and the second inner wall 12b face each other in the Y direction, and the third inner wall 12c and the fourth inner wall 12d face each other in the X direction.

A thickness T1 of the filter base portion 12 in the filter portion 10 is equal to or more than 0.5 μm and equal to or less than 20 μm. With such a configuration, it is possible to reduce pressure loss of a fluid passing through the filter while providing mechanical strength. Preferably, the thickness T1 of the filter base portion 12 in the filter portion 10 is equal to or more than 1.0 μm and equal to or less than 3 μm. With such a configuration, the pressure loss of the fluid passing through the filter can be further reduced.

As illustrated in FIG. 3B, a first opening 11a of the through-hole 11 is formed on the first main surface PS1 side of the filter portion 10. In addition, a second opening 11b of the through-hole 11 is formed on the second main surface PS2 side of the filter portion 10. In Embodiment 1, the first opening 11a and the second opening 11b each have a square shape when viewed from the first main surface PS1 side.

The first opening 11a has a dimension C1 and the second opening 11b has a dimension C2. The dimension C1 of the first opening 11a and the dimension C2 of the second opening 11b are representative dimensions in the shape of the opening. In Embodiment 1, each of the dimensions C1 and C2 may be one side of the square shape. Alternatively, for example, when the shapes of the first opening 11a and the second opening 11b are circular shapes, the dimensions C1 and C2 may be diameters.

For example, the dimension C1 of the first opening 11a and the dimension C2 of the second opening 11b are 0.5 μm to 400 μm. Preferably, the dimension C1 of the first opening 11a and the dimension C2 of the second opening 11b are 1 μm to 30 μm. In Embodiment 1, the dimension C1 of the first opening 11a and the dimension C2 of the second opening 11b are the same.

Note that the shape of the first opening 11a and the second opening 11b is not limited to a square shape. For example, the shape of the first opening 11a and the second opening 11b may be a circular shape, an elliptical shape, a rectangular shape, a polygonal shape, or the like.

In the filter portion 10, the first main surface PS1 and the second main surface PS2 preferably have small surface roughness. Here, the surface roughness means an average value of differences between a maximum value and a minimum value measured by a contact surface profiler at arbitrary five points. In Embodiment 1, the surface roughness is preferably smaller than the size of the filtration object, and more preferably smaller than half the size of the filtration object. This is because adhesion of the filtration object is reduced, and the filtration object can be collected with high efficiency after being captured by the filter.

Returning to FIG. 1, the support portion 13 is arranged on the first main surface PS1 of the filter portion 10. In other words, the support portion 13 is arranged on the first main surface PS1 of the filter base portion 12.

The support portion 13 is formed in a lattice shape. Specifically, the support portion 13 includes a plurality of first support members 13*a* extending in the first direction (X direction) and a plurality of second support members 13*b* extending in the second direction (Y direction) intersecting the first direction. In Embodiment 1, the first direction is the X direction, and the second direction is the Y direction. That is, the plurality of first support members 13*a* and the plurality of second support members 13*b* are orthogonal to each other. In addition to the above description, in Embodiment 1, the first support member 13*a* and the first base member 12*aa* extend parallel to each other, and the second support member 13*b* and the second base member 12*ba* extend parallel to each other.

The plurality of first support members 13*a* and the plurality of second support members 13*b* are formed of plate-shaped members. The plurality of first support members 13*a* and the plurality of second support members 13*b* are integrally formed.

The plurality of first support members 13*a* and the plurality of second support members 13*b* are arranged at equal intervals. For example, an interval A1, respectively, of the plurality of first support members 13*a* and the plurality of second support members 13*b* is 200 μm to 500 μm. Preferably, the interval A1 is 250 μm to 350 μm. The number of through-holes 11 blocked by the support portion 13 is reduced, and mechanical strength is obtained.

When the filter portion 10 is viewed from the first main surface PS1 side, a width B1 of each of the plurality of first support members 13*a* and the plurality of second support members 13*b* is larger than the width of each of the plurality of first base members 12*aa* and the plurality of second base members 12*ba* of the filter base portion 12. For example, the width B1 of each of the plurality of first support members 13*a* and the plurality of second support members 13*b* is 5 μm to 40 μm. Preferably, the width B1 is 10 μm to 25 μm. The mechanical strength of the filter 1 is obtained by the support portion 13.

Figure 4:
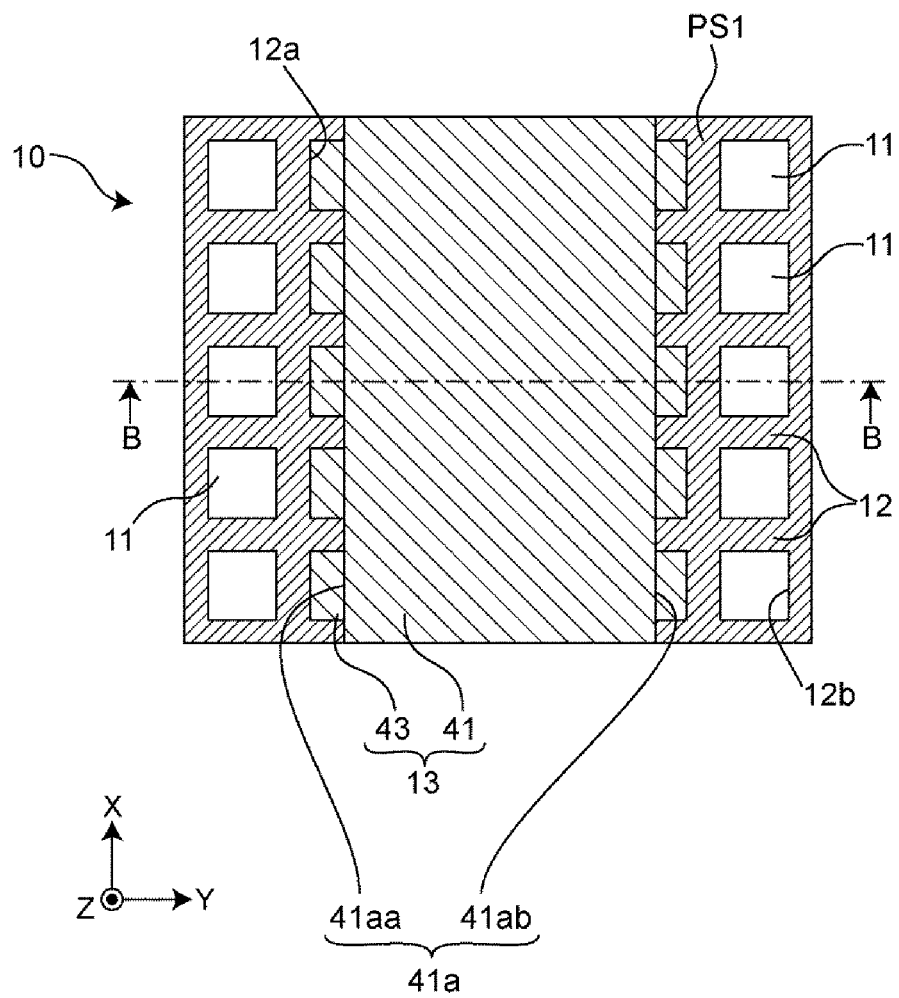
FIG. 4 is an enlarged view of a part of a filter base portion in which a support portion is arranged.
Figure 5:
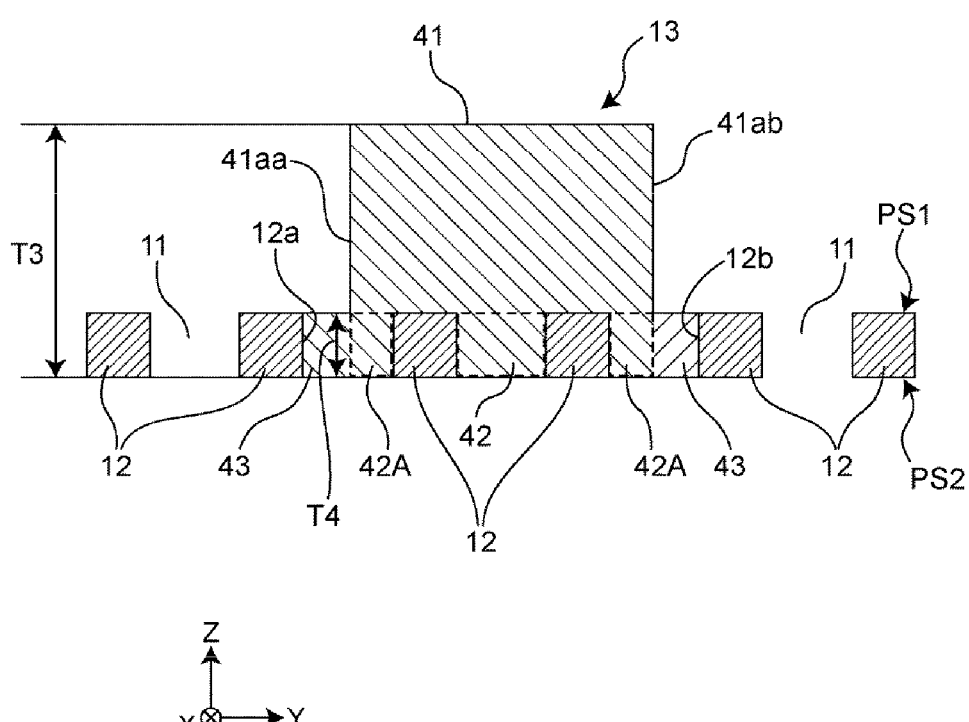
FIG. 5 is a cross-sectional view taken along a line B-B of FIG. 4.

FIG. 4 is an enlarged view of a part of the filter base portion 12 in which the support portion 13 is arranged. FIG. 5 is an enlarged cross-sectional view of the support portion 13 taken along a line B-B of FIG. 4.

As illustrated in FIG. 4, the support portion 13 includes a main body portion 41 and a plurality of protruding portions 43. The main body portion 41 has a sidewall 41*a*, and more specifically, has a first sidewall 41*aa* and a second sidewall 41*ab* facing the first sidewall 41*aa*. The main body portion 41 is arranged so as to cover a part or all of the plurality of through-holes 11, and the plurality of protruding portions 43 are arranged so as to protrude from the sidewall 41*a* of the main body portion 41. To be more specific, the plurality of protruding portions 43 protrude in the −Y direction from the first sidewall 41*aa* side of the main body portion 41 toward the first inner wall 12*a*, and protrude in the +Y direction from the second sidewall 41*ab* side of the main body portion 41 toward the second inner wall 12*b*.

As illustrated in FIG. 5, the main body portion 41 is arranged on the first main surface PS1, protrudes from the first main surface PS1 toward the +Z direction, and has the sidewall 41*a* along the Z direction. In this specification, the term "along" is not limited to a state of being parallel to a certain direction but means a state of being formed in the vicinity of a plane parallel to the certain direction. The upper surface of the main body portion 41 may form a flat surface or a curved surface orthogonal to the Z direction.

Further, the main body portion 41 includes a plurality of fixing portions 42 arranged in the plurality of through-holes 11. The fixing portions 42 extend from the first main surface PS1 toward the second main surface PS2. As illustrated in FIG. 5, the fixing portions 42 have a prismatic shape. The fixing portions 42 are arranged in the through-hole 11 and may be embedded in the through-hole 11. In the present specification, "being embedded" means that the volume of the object for embedding substantially matches the volume of the content to be embedded. When the embedded fixing portions 42 are formed, close contact property of the support portion 13 with respect to the filter base portion 12 is improved. On the other hand, among the plurality of fixing portions 42, a fixing portion 42A located on the sidewall 41*a* side of the main body portion 41 is not embedded in the through-hole 11. The fixing portion 42A is formed in a part of the through-hole 11, and the first main surface PS1 and the second main surface PS2 partially communicate with each other in the through-hole 11 in which the fixing portion 42A is arranged. Therefore, in the through-hole 11 in which the fixing portion 42A is arranged, the volume formed by the through-hole 11 is partially filled to form an incomplete through-hole 11.

The number of the fixing portions 42 and 42A to be formed can be arbitrarily set depending on the dimensions of the through-hole 11, the filter base portion 12, and the support portion 13, and the extending direction of the filter base portion 12 and the support portion 13.

A thickness T3 of the main body portion 41 is a thickness along the Z direction from the second main surface PS2 to the protruding upper surface of the main body portion 41. The thickness T3 is, for example, 5 μm to 40 μm. Preferably, the thickness T3 of the main body portion 41 is 10 μm to 25 μm.

As illustrated in FIG. 5, the protruding portion 43 protrudes from the fixing portion 42A located on the sidewall 41*a* side of the main body portion 41 toward the outer side portion relative to the main body portion 41 in the direction along the first main surface PS1. In Embodiment 1, the protruding portion 43 is provided at each of the fixing portions 42A located on the first sidewall 41*aa* side and the second sidewall 41*ab* side, and protrudes in the Y direction. The protruding portion 43 is in contact with the first inner wall 12*a* of the through-hole 11 in which the fixing portion 42A located on the first sidewall 41*aa* side of the main body portion 41 is arranged. Further, the protruding portion 43 is in contact with the second inner wall 12*b* of the through-hole 11 in which the fixing portion 42A located on the second sidewall 41*ab* side of the main body portion 41 is arranged. That is, the protruding portion 43 is in contact with the fixing portion 42A and the inner walls 12*a* and 12*b* adjacent to the fixing portion 42A with an interval. The protruding portion 43 may be in full or partial contact with the respective inner walls 12*a* and 12*b*. For example, the end surface of the protruding portion 43 and the inner walls 12*a* and 12*b* roughly match and are in close contact with each other.

Further, the protruding portion 43 may seal the through-hole 11 in which the fixing portion 42A is arranged. In this specification, "sealing" includes entirely blocking the through-hole 11, but is not limited to the case where the through-hole 11 is filled, and also includes partially blocking the through-hole 11. Therefore, the total volume of one protruding portion 43 and one fixing portion 42A may be smaller than the volume of one through-hole 11.

In Embodiment 1, the protruding portion 43 has a surface continuous with the first main surface PS1. In other words, the protruding portion 43 forms a flat surface together with the first main surface PS1 without forming a step along the extending direction of the first main surface PS1.

A thickness T4 of the protruding portion 43 is the thickness along the Z direction from the second main surface PS2 to the end portion of the protruding portion 43 on the first main surface PS1 side. The thickness T4 is smaller than the thickness T3 of the main body portion 41. The thickness T4 is, for example, 0.5 μm to 20 μm. Preferably, the thickness T4 of the protruding portion 43 is 1.0 μm to 3 μm.

It is preferable that the thermal expansion coefficient of the material forming the filter base portion 12 and the thermal expansion coefficient of the material forming the support portion 13 be substantially equal to each other. Here, "substantially equal" includes errors within 15%.

For example, the filter base portion 12 and the support portion 13 may be formed of a material of Ni or PdNi (Pd ratio: 50% to 95%). For example, the filter base portion 12 may be formed of Ni, and the support portion 13 may be formed of PdNi. Note that the combination of materials of the filter base portion 12 and the support portion 13 is not limited thereto.

[Manufacturing Method of Filter]

An example of a method for manufacturing the filter 1 will be described with reference to FIGS. 6A to 6G. FIGS. 6A to 6G are schematic views illustrating an example of a manufacturing process of the filter 1 of Embodiment 1 according to the present invention.

Figure 6A:
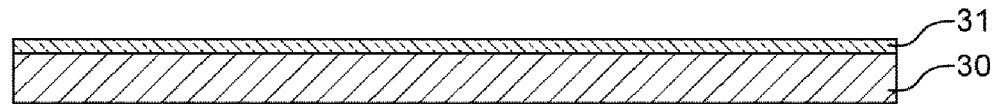
FIG. 6A is a schematic view illustrating an example of a manufacturing process of the filter of Embodiment 1 according to the present invention.

As illustrated in FIG. 6A, a Cu film 31 is formed on a substrate 30. For example, the Cu film 31 is formed by sputtering using a sputtering film forming apparatus. Alternatively, the Cu film 31 may be formed by vapor deposition using a vapor deposition apparatus. At this time, in order to improve adhesion between the substrate 30 and the Cu film 31, a Ti film may be formed between the substrate 30 and the Cu film 31.

Figure 6B:
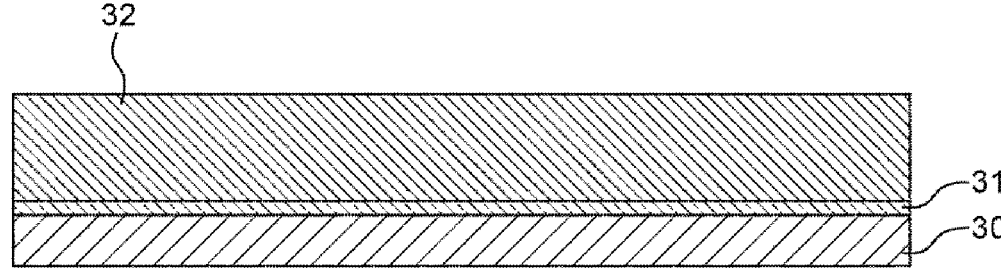
FIG. 6B is a schematic view illustrating an example of the manufacturing process of the filter of Embodiment 1 according to the present invention.

As illustrated in FIG. 6B, a resist is applied onto the Cu film 31 and dried to form a resist film 32. For example, a photosensitive positive liquid resist is applied onto the Cu film 31 by using a spin coater.

Figure 6C:
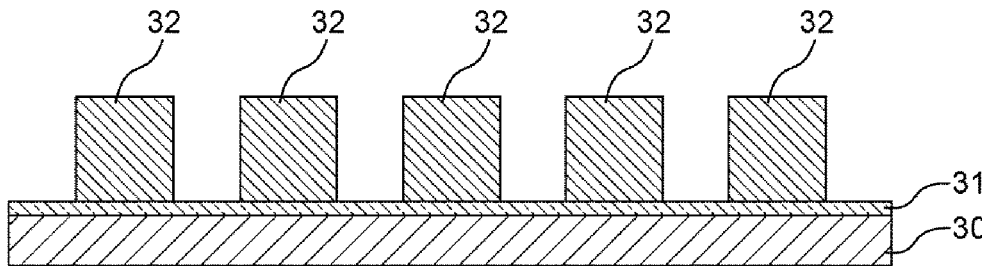
FIG. 6C is a schematic view illustrating an example of the manufacturing process of the filter of Embodiment 1 according to the present invention.

As illustrated in FIG. 6C, the resist film 32 is subjected to exposure and development processing to remove the resist film 32 at a position corresponding to the filter base portion 12. In the exposure conditions, by setting the focus on the plus side relative to an appropriate value, the cross-sectional shape of the resist film 32 becomes a trapezoidal shape.

Development is carried out using a paddle development apparatus. Tetramethylammonium hydroxide (TMAH) is used as a developing solution.

After exposure and development processing, washing with water and drying treatment are carried out.

Figure 6D:
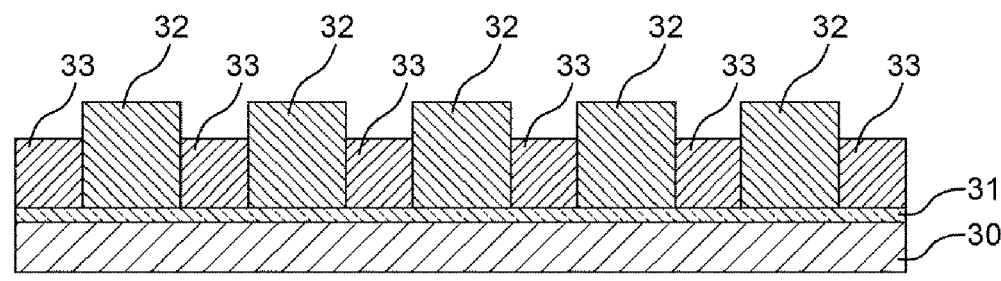
FIG. 6D is a schematic view illustrating an example of the manufacturing process of the filter of Embodiment 1 according to the present invention.

As illustrated in FIG. 6D, electrolytic plating is performed using an electrolytic plating apparatus. As such, a plating film 33 is formed in the portion from which the resist film 32 has been removed.

Figure 6E:
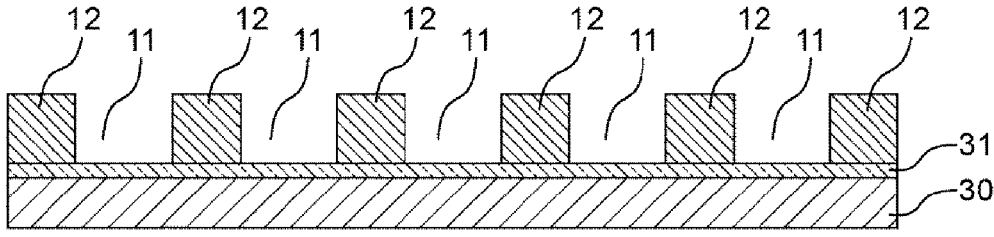
FIG. 6E is a schematic view illustrating an example of the manufacturing process of the filter of Embodiment 1 according to the present invention.

As illustrated in FIG. 6E, the resist film 32 is stripped with a stripping solution. As a result, the filter base portion 12 in which the plurality of through-holes 11 is formed is formed.

Figure 6F:
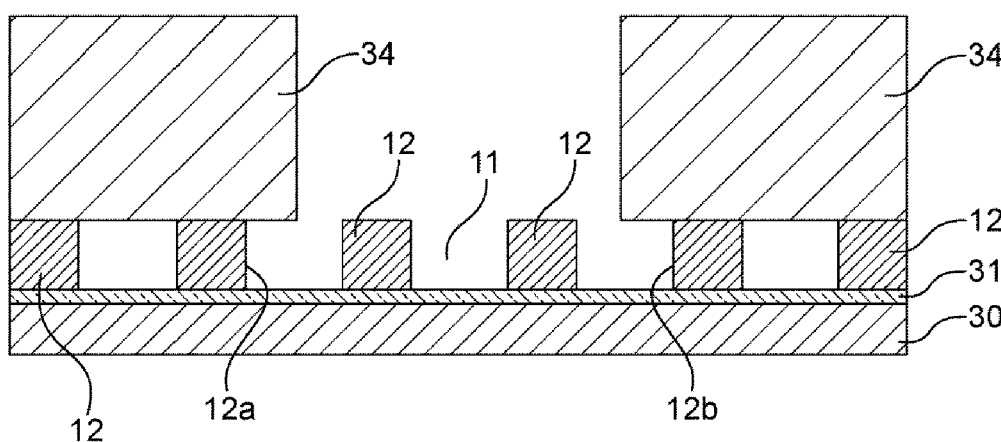
FIG. 6F is a schematic view illustrating an example of the manufacturing process of the filter of Embodiment 1 according to the present invention.

As illustrated in FIG. 6F, a resist 34 is formed on the filter base portion 12. As the resist 34, for example, a photosensitive dry film resist having a thickness of 25 μm may be used. Due to rigidity of the resist 34, the resist 34 can be prevented from entering the through-hole 11.

Alternatively, the resist 34 may be attached to the filter base portion 12 by lamination using a roller.

Then, the resist 34 is subjected to exposure and development processing, and the resist 34 at a position corresponding to the support portion 13 is removed.

Figure 6G:
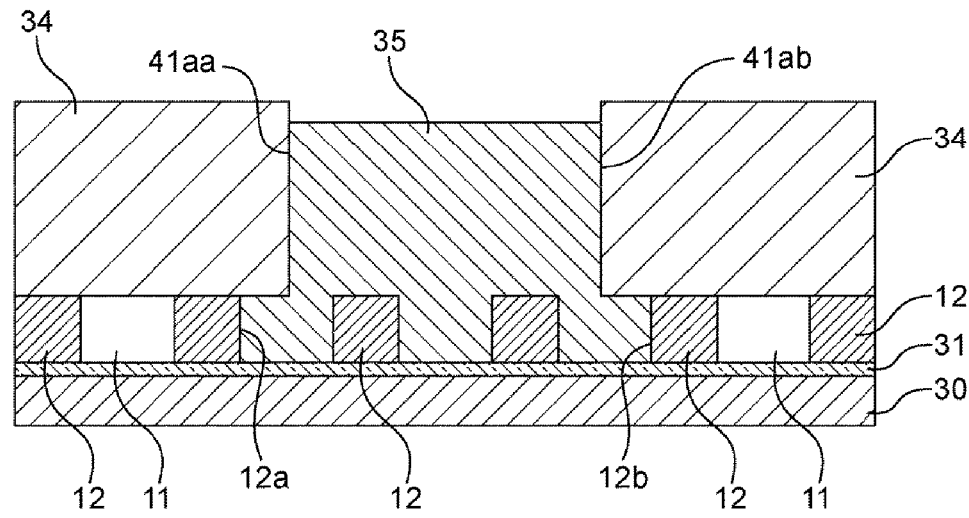
FIG. 6G is a schematic view illustrating an example of the manufacturing process of the filter of Embodiment 1 according to the present invention.

As illustrated in FIG. 6G, electrolytic plating is performed using an electrolytic plating apparatus. As such, a plating film 35 is formed at a portion corresponding to the support portion 13, that is, a portion in which the resist 34 is not formed. Since the through-hole 11 is not filled with the resist 34, the plating film 35 can flow into the through-hole 11 and comes into contact with the inner walls 12*a* and 12*b*.

Although not illustrated, the resist 34 is removed by using alkali after the electrolytic plating. Thereafter, the Cu film 31 is removed by etching.

In this manner, the filter 1 can be produced.

[Operation]

Figure 7:
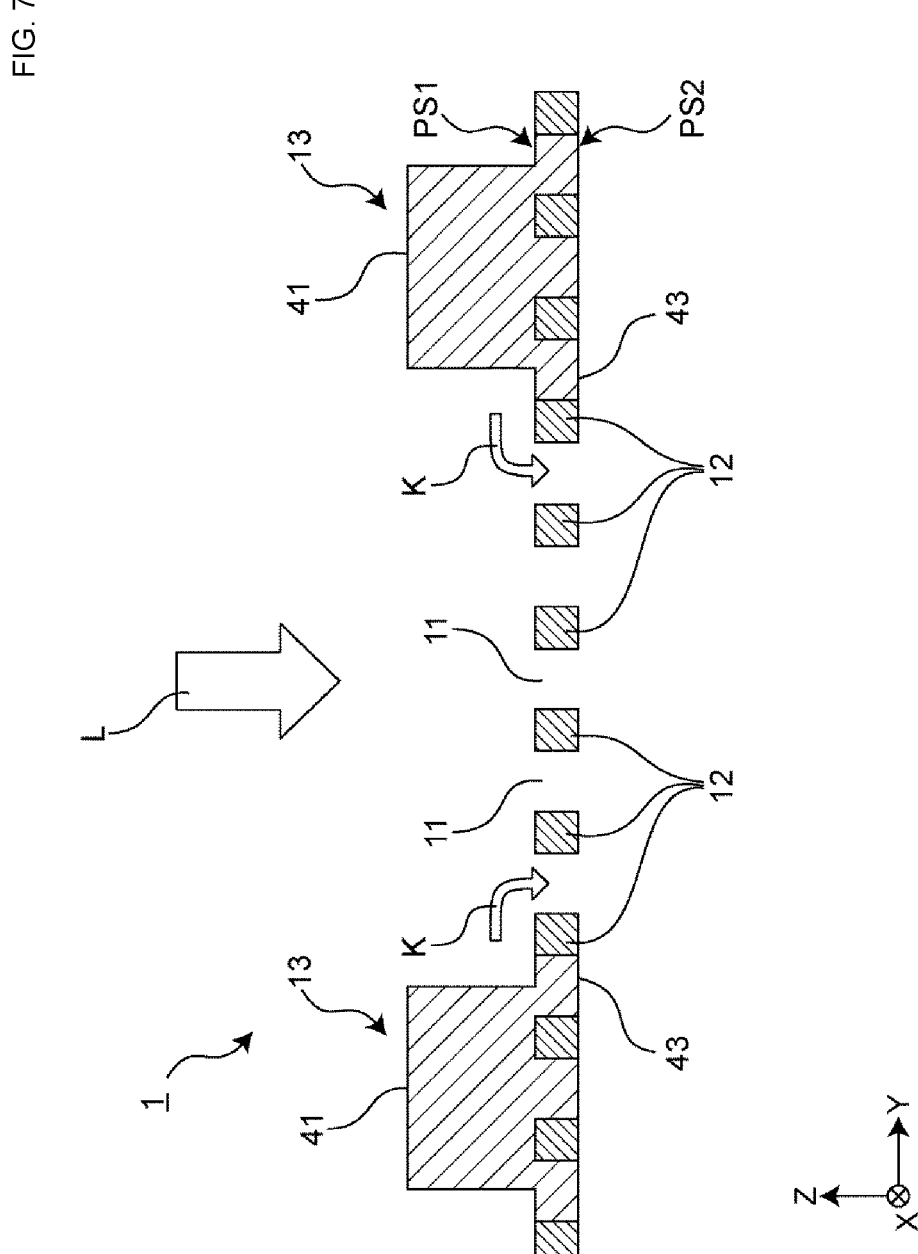
FIG. 7 is a cross-sectional view illustrating a part of the filter of Embodiment 1 according to the present invention.

An example of the operation of the filter 1 will be described with reference to FIG. 7. FIG. 7 is a cross-sectional view illustrating a part of the filter 1 of Embodiment 1 according to the present invention.

The fluid containing the filtration object flows through the filter 1 in the direction indicated by an arrow L, that is, in the direction from the first main surface PS1 toward the second main surface PS2. The filtration object is captured by the filter base portion 12 and held on the first main surface PS1. On the other hand, the fluid passes through the through-hole 11 and is discharged from the second main surface PS2 side. A part of the fluid may be maintained on the protruding portion 43, and the fluid accumulates in the vicinity of the support portion 13. In addition, impurities contained in the fluid flowing on the protruding portion 43 of the support portion 13 do not accumulate in the vicinity of the support portion 13, but move on the protruding portion 43 and the filter base portion 12 along an arrow K and pass through the through-hole 11.

Effects

According to the filter 1 according to Embodiment 1, the following effects can be obtained.

The filter 1 includes the filter base portion 12 having the first main surface PS1 and the second main surface PS2, in which the plurality of through-holes 11 is formed, and the support portion 13 arranged at the filter base portion 12. The through-hole 11 communicates between the first main surface PS1 and the second main surface PS2. The support portion 13 includes the main body portion 41 and the protruding portion 43. The main body portion 41 is arranged on the first main surface PS1 and includes the plurality of fixing portions 42 and 42A arranged in the plurality of through-holes 11. The protruding portion 43 protrudes from the fixing portion 42A located at the sidewall 41*a* side of the main body portion 41 toward the outer side portion of the main body portion 41 in the Y direction along the first main surface PS1. In addition, the thickness T4 of the protruding portion 43 is smaller than the thickness T3 of the main body portion 41.

Here, the configuration of a filter in the past will be described. In the vicinity of the incomplete through-hole 11 in the filter in the past, the cross-sectional area of the flow path decreases and the fluid velocity increases, so that the pressure decreases. Due to the decrease in pressure, the filtration object and the fluid are sacked, in particular, towards the incomplete through-hole 11. The "incomplete through-hole 11" in Embodiment 1 means the through-hole 11 having an opening dimension smaller than the dimension C1. In addition, when the filtration object is a cell, the filtration object is likely to be deformed. When the filtration object larger than the through-hole 11 is filtered, the filtration object is deformed, and likely to be sucked in to clog the incomplete through-hole 11 in the vicinity of the support portion 13.

On the other hand, according to such a configuration of the present invention, the opening area of the filter 1 due to the incomplete through-hole 11 is reduced by the arrangement of the protruding portion 43 in the through-hole 11 in which the fixing portion 42A is arranged. Therefore, in filtration using the filter 1, the amount of the filtration object entering and clogging the incomplete through-hole 11 is reduced, and clogging of the through-hole 11 can be prevented. As a result, it is possible to collect a larger amount of the filtration object. In a case where the filtration object is a cell, in the filtration using the filter 1, the cell is not deformed and does not clog the incomplete through-hole 11, and thus a larger amount of the cell can be collected.

The filter base portion 12 has the inner walls 12a and 12b extending from the second main surface PS2 toward the first main surface PS1 and defining the plurality of through-holes 11. The protruding portion 43 is in contact with the first inner wall 12a and the second inner wall 12b of the through-hole 11 in which the fixing portion 42A located on the sidewall 41a side of the main body portion 41 is arranged.

With such a configuration, it is possible to further prevent the filtration object from entering the through-hole 11 in which the fixing portion 42A is arranged, and thus it is possible to further suppress the filtration object from causing clogging.

The protruding portion 43 has a surface continuous with the first main surface PS1.

With such a configuration, the surface of the protruding portion 43 on the first main surface PS1 side and the first main surface PS1 form a flat surface. In other words, no surface structure that obstructs the discharge of the object, such as a step, is formed between the surface of the protruding portion 43 and the first main surface PS1. As such, the filtration object is held on the first main surface PS1 without being caught by the surface structure, and can be easily recovered. Furthermore, when a fluid containing impurities other than the filtration object is filtered using the filter 1, the impurities precipitated on the protruding portion 43 is moved on the filter base portion 12 continuous with the protruding portion 43 and can be discharged through the through-hole 11.

The protruding portion 43 seals the through-hole 11 in which the fixing portion 42A located on the sidewall 41a side of the main body portion 41 is arranged.

With such a configuration, it is possible to further prevent the filtration object from entering the through-hole 11 in which the fixing portion 42A is arranged.

Further, by filling the through-hole 11 with the protruding portion 43, communication between the first main surface PS1 and the second main surface PS2 can be blocked in the vicinity of the protruding portion 43. As a result, when the fluid containing the filtration object is filtered by using the filter 1, the fluid that normally passes through the through-hole 11 and is discharged from the second main surface PS2 side is held on the first main surface PS1 by the protruding portion 43. Therefore, it resulted in a liquid film formed in the vicinity of the support portion 13, and when the filtration object is a cell, it is possible to prevent drying and death of the cell and collect a larger number of cells in a viable state.

In addition, when the fluid containing the filtration object is filtered by using the filter 1, a flow in the Y direction is generated in the vicinity of the protruding portion 43, the filtration object held on the through-hole 11 and the first main surface PS1 is separated (floated), and it is possible to reduce clogging. Therefore, in particular, when the filtration object is cells, the cells are not pressed against the through-hole 11 and the first main surface PS1 for a long time, and stress applied to the cells can be reduced.

The protruding portions 43 each are arranged on the first sidewall 41aa side and the second sidewall 41ab side of the main body portion 41.

With such a configuration, it is possible to further prevent the filtration object and the fluid from entering the through-hole 11 in which the fixing portion 42A is arranged.

The support portion 13 includes the plurality of first support members 13a extending in the first direction (X direction) and the plurality of second support members 13b extending in the second direction (Y direction) intersecting the first direction. Each of the first support member 13a and the second support member 13b includes the main body portion 41 and the protruding portion 43.

With such a configuration, strength of the filter 1 can be improved.

The size of the through-holes 11 can be made more uniform by the protruding portion 43. Therefore, when an electromagnetic wave (particularly, visible light) is incident on the filter 1, the slit width (through-hole 11) becomes uniform in transmission of the electromagnetic wave, so that electromagnetic wave interference between the plurality of slits efficiently occurs, and the electromagnetic wave interference intensity of the electromagnetic wave transmitted through the filter 1 can be increased. By using a strong interference electromagnetic wave, the filter 1 itself and the substance captured by the filter 1 can be easily observed. Note that this phenomenon also occurs in the reflection on the side on which the electromagnetic wave is incident.

Note that although an example in which the first support member 13a and the first base member 12aa extend parallel to each other and the second support member 13b and the second base member 12ba extend parallel to each other has been described in Embodiment 1, the present invention is not limited to this. The first support member 13a and the first base member 12aa may extend in different directions with respect to each other.

Note that although an example in which the first direction in which the first support member 13a and the first base member 12aa extend is orthogonal to the second direction in which the second support member 13b and the second base member 12ba extend has been described in Embodiment 1, the present invention is not limited thereto. The first direction and the second direction may have arbitrary relationship in a plane in which the filter base portion 12 is formed. For example, the plurality of first support members 13a and the plurality of first base members 12aa may be formed on a concentric circle with respect to the circle of the filter 1, and the second support member 13b and the second base member 12ba may be formed along a radial direction with respect to the circle.

Note that in Embodiment 1, an example in which the dimension C1 of the first opening 11*a* is the same as the dimension C2 of the second opening 11*b* has been described, but the present invention is not limited thereto. The dimension C2 of the second opening 11*b* may be larger than the dimension C1 of the first opening 11*a*. In such a configuration, the support portion 13 is less likely to come off from the filter base portion 12.

Note that in Embodiment 1, an example in which the protruding portion 43 completely plugs the through-hole 11 in which the fixing portion 42A is arranged has been described, but the present invention is not limited thereto. For example, the support portion 43 may protrudes relative to the fixing portion 42A in the direction (Y direction) along the first main surface PS1, and the through-hole 11 may partially communicate from the first main surface PS1 to the second main surface PS2. Even in such a configuration, it is possible to reduce the opening area of the through-hole 11 in the first main surface PS1 and to prevent clogging.

Note that in Embodiment 1, an example in which the protruding portion 43 protrudes in the Y direction and comes into contact with the first inner wall 12*a* and the second inner wall 12*b* of the through-hole 11 has been described, but the present invention is not limited thereto. For example, the protruding portion 43 may protrude in the X direction from the fixing portion 42A so as to be in contact with the third inner wall 12*c* and the fourth inner wall 12*d*. Even in such a configuration, it is possible to reduce the opening area of the through-hole 11 in the first main surface PS1 and to prevent clogging.

Note that in Embodiment 1, an example in which the fixing portions 42 and 42A have a prismatic shape has been described, but the present invention is not limited thereto. The fixing portions 42 and the 42A may have a shape other than a pyramidal shape in accordance with the shape of the through-hole 11. For example, when the through-hole 11 has a circular shape, the fixing portion 42 has a circular shape and the fixing portion 42A has a semicircular shape. In such a configuration, the support portion 13 is more firmly fixed to the filter base portion 12, and the close contact property of the support portion 13 can be improved.

Note that in Embodiment 1, an example in which the protruding portion 43 and the first main surface PS1 form the flat surface has been described, but the present invention is not limited thereto. As in Modification 1 and Modification 2 described later, the protruding portion 43 may protrude or be recessed with respect to the first main surface PS1.

[Modification 1]

Figure 8A:
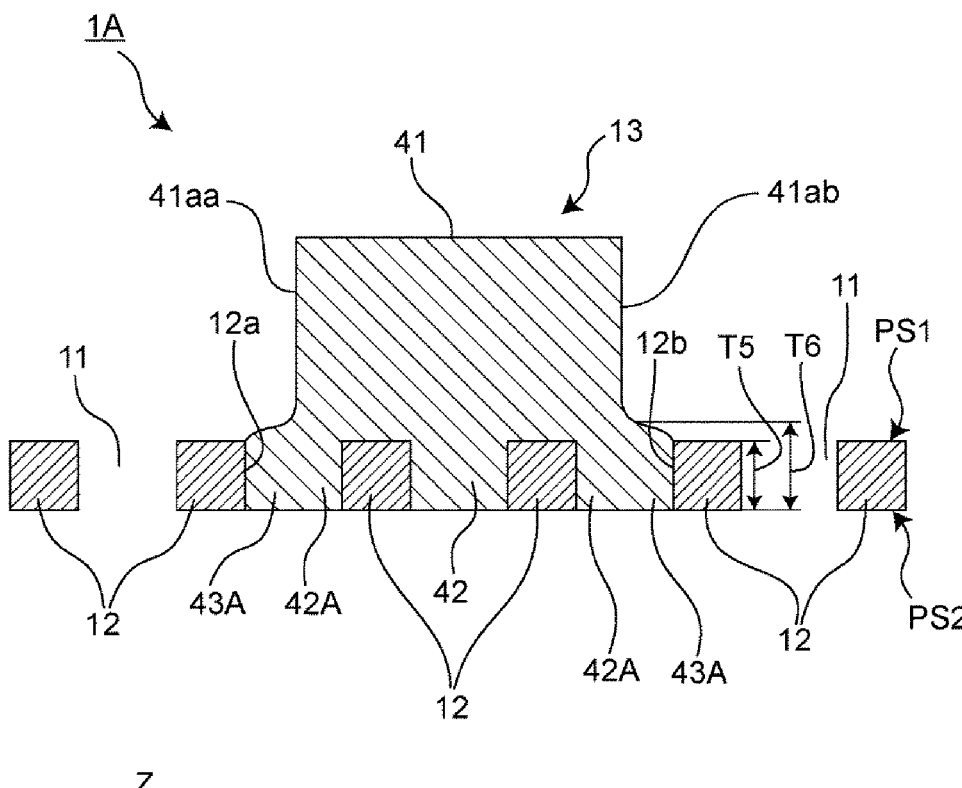
FIG. 8A is an enlarged cross-sectional view of a support portion of a modification of Embodiment 1 according to the present invention.
Figure 8A:
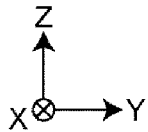

FIG. 8A illustrates a part of a filter 1A of a modification of Embodiment 1. As illustrated in FIG. 8A, the support portion 13 of the filter 1A includes a protruding portion 43A. The protruding portion 43A has a shape protruding from the first main surface PS1, from the second main surface PS2 toward the first main surface PS1 (in the Z direction). Further, a thickness T6 of the protruding portion 43A at a position in contact with the main body portion 41 is larger than a thickness T5 of the protruding portion 43A at a position in contact with the inner wall 12*b*. The thicknesses T5 and T6 are thicknesses measured along the Z direction from the second main surface PS2 to the upper surface of the protruding portion 43A, and may be constant in the support portion 13 or may be different depending on the protruding portion 43A. In Modification 1, the other configurations of the filter 1A are the same as those of the filter 1 of Embodiment 1.

The surface of the protruding portion 43A on the first main surface PS1 side may be an inclined surface extending from the sidewall 41*a* of the main body portion 41 or may be curved to have a convex shape. In addition, the surface of the protruding portion 43A on the first main surface PS1 side may have a concave portion or a recess in the +Z direction relative to the first main surface PS1. The protruding shape of the protruding portion 43A protrudes in a range of a few μm or several tens of μm with respect to the first main surface PS1.

With such a configuration, it is possible to prevent the filtration object or a substance such as impurities requested to be separated from the filtration object from entering the through-hole 11 in the vicinity of the support portion 13. Further, it is possible to promote the movement of the impurities to other through-holes 11. The impurities arranged on the convex shape move from the protruding portion 43A to the through-hole 11 toward the first main surface PS1 of the filter base portion 12. In particular, since the thickness T6 of the protruding portion 43A is larger than the thickness T5 of the protruding portion 43A, the impurities move, from the position of the thickness T6 to the position of the thickness T5, to the through-hole 11 away from the main body portion 41. Thus, the impurities can be discharged from the top of the filter 1A. Similarly, the fluid and its droplets can also be discharged from the top of the filter 1A.

[Modification 2]

Figure 8B:
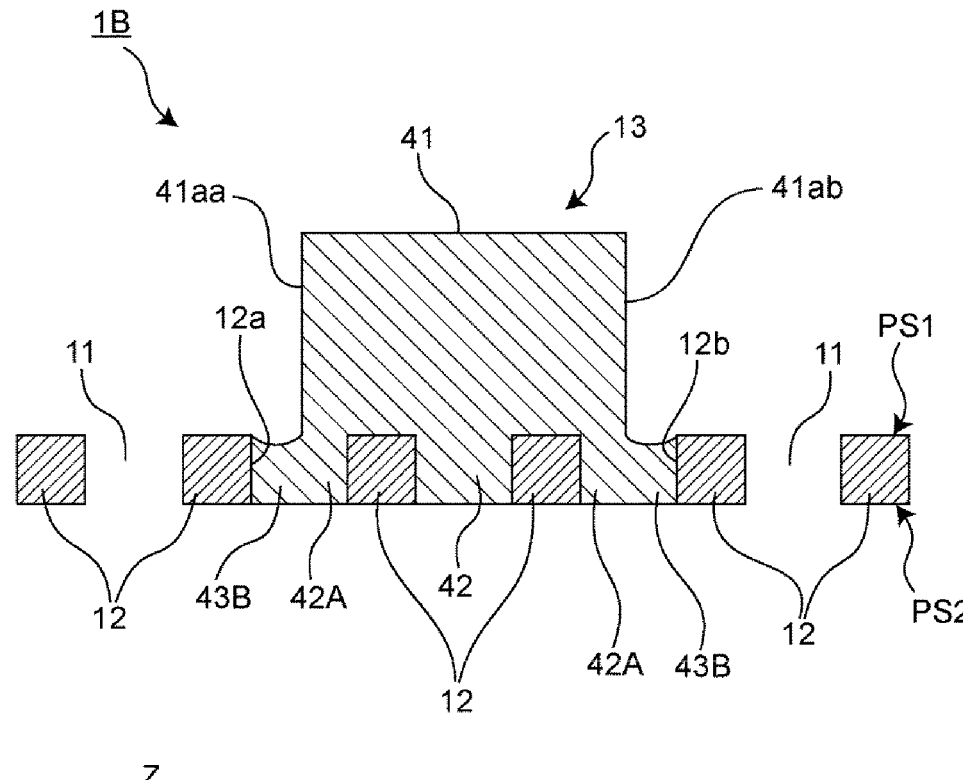
FIG. 8B is an enlarged cross-sectional view of a support portion of a modification of Embodiment 1 according to the present invention.

FIG. 8B illustrates a part of a filter 1B of a modification of Embodiment 1. As illustrated in FIG. 8B, the support portion 13 of the filter 1B includes a protruding portion 43B. The protruding portion 43B has a shape recessed with respect to the first main surface PS1 from the first main surface PS2 toward the second main surface PS1 (in the Z direction). In Modification 2, the other configurations of the filter 1B are the same as those of the filter 1 of Embodiment 1.

The surface of the protruding portion 43B on the first main surface PS1 side may be an inclined surface extending from the sidewall 41*a* of the main body portion 41 or may be curved to have a concave shape. In addition, the surface of the protruding portion 43A on the first main surface PS1 side may have a convex shape on the −Z direction side relative to the first main surface PS1. The recessed shape of the protruding portion 43B is recessed in a range of a few μm or several tens of μm with respect to the first main surface PS1.

With such a configuration, the liquid can be held in the recess of the protruding portion 43B to form a liquid pool. Cells may be held in the liquid pool. As a result, drying of the filtration object such as cells accumulated in the vicinity of the support portion 13 can be suppressed. Further, the cells can be collected in the recess of the protruding portion 43B.

Note that in Embodiment 1, an example in which the protruding portion 43 is arranged so as to protrude from both sides of the main body portion 41 has been described, but the present invention is not limited thereto. As in Modification 3 described later, the protruding portion 43 may protrude to one side of the main body portion 41.

[Modification 3]

Figure 9:
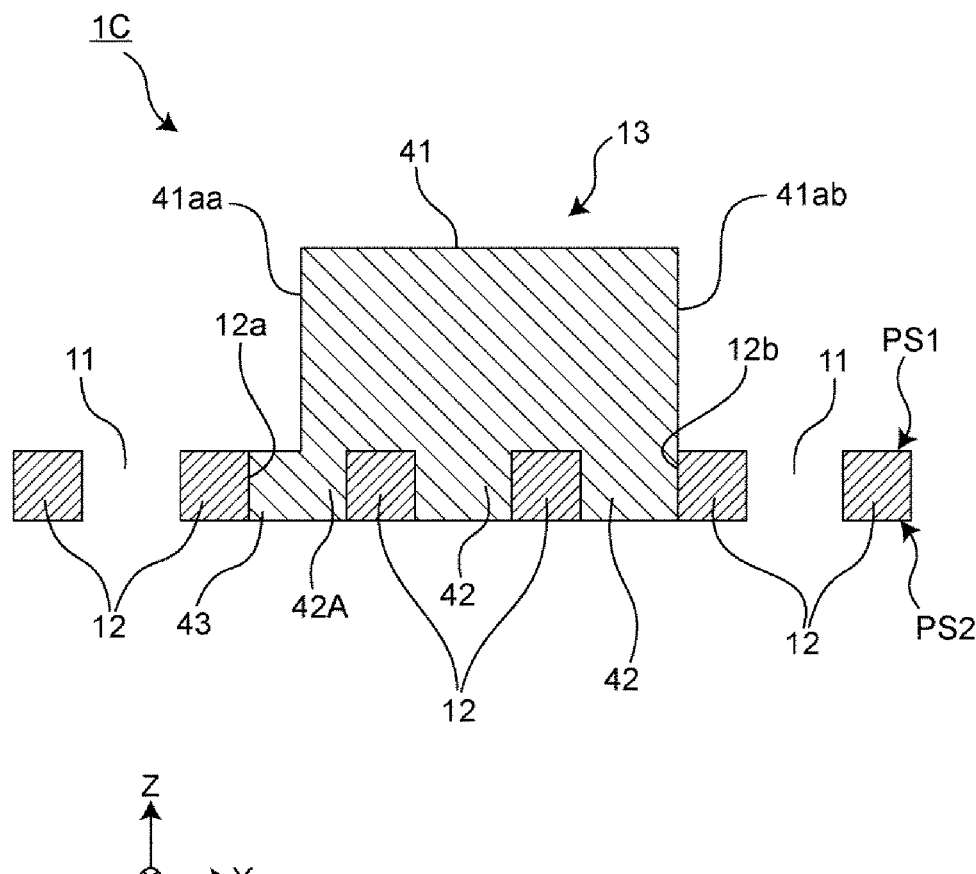
FIG. 9 is an enlarged cross-sectional view of a support portion of a modification of Embodiment 1 according to the present invention.

FIG. 9 illustrates a part of a filter 1C of a modification of Embodiment 1. As illustrated in FIG. 9, the support portion 13 of the filter 1C includes the main body portion 41 and one protruding portion 43 protruding in the −Y direction. To be more specific, the protruding portion 43 is formed only between the fixing portion 42A extended from the first sidewall 41*aa* and the first inner wall 12*a*. On the other hand, the second sidewall 41*ab* of the main body portion 41 is in contact with the second inner wall 12*b*, and the protruding portion 43 is not formed between the second sidewall 41*ab* and the second inner wall 12*b*.

With such a configuration as well, it is possible to reduce the number of incomplete through-holes 11 and prevent clogging of the through-holes 11. Note that in Modification 3, an example in which one protruding portion 43 protrudes in the −Y direction has been described, but the present invention is not limited thereto. For example, the support portion 13 may include one protruding portion 43 that protrudes from the fixing portion 42A extended from the second sidewall 41*ab* toward the second inner wall 12*b* in the +Y direction.

Although the present invention has been fully described in connection with the preferred embodiments with reference to the accompanying drawings, various changes and modifications will become apparent to those skilled in the art. Such changes and modifications are to be understood as included within the scope of the present invention as defined by the appended claims unless they depart therefrom.

Since the clogging can be prevented, the filter of the present invention is useful for filtration of a fluid containing a filtration object.

REFERENCE SIGNS LIST

1 FILTER
10 FILTER PORTION
11 THROUGH-HOLE
12 FILTER BASE PORTION
12*a*, 12*b*, 12*c*, 12*d* INNER WALL
12*aa* FIRST BASE MEMBER
12*ba* SECOND BASE MEMBER
13 SUPPORT PORTION
13*a* FIRST SUPPORT MEMBER
13*b* SECOND SUPPORT MEMBER
20 FRAME PORTION
30 SUBSTRATE
31 Cu FILM
32 RESIST FILM
33 PLATING FILM
34 RESIST
35 PLATING FILM
41 MAIN BODY PORTION
41*a* SIDEWALL
42, 42A FIXING PORTION
43 PROTRUDING PORTION
PS1 FIRST MAIN SURFACE
PS2 SECOND MAIN SURFACE

The invention claimed is:

1. A filter comprising:
  a filter base portion having a first main surface and a second main surface opposite to the first main surface, the filter base portion defining a plurality of through-holes communicating between the first main surface and the second main surface; and
  a support portion arranged on the filter base portion, wherein the support portion includes:
    a main body portion on the first main surface and including a plurality of fixing portions in some of the plurality of through-holes; and
    a protruding portion protruding toward an outer side portion of the main body portion in a direction along the first main surface from a fixing portion located on a sidewall side of the main body portion among the plurality of fixing portions, and
  a thickness of the protruding portion is smaller than a thickness of the main body portion.

2. The filter according to claim 1, wherein the thickness of the protruding portion is 0.5 μm to 20 μm.

3. The filter according to claim 1,
  wherein the filter base portion has an inner wall extending from the second main surface toward the first main surface and which defines the plurality of through-holes, and
  the protruding portion is in contact with the inner wall of a through-hole of the plurality of through-holes in which the fixing portion located on the sidewall side of the main body portion is arranged.

4. The filter according to claim 3, wherein the protruding portion has a surface continuous with the first main surface.

5. The filter according to claim 3, wherein the protruding portion has a surface protruding above the first main surface.

6. The filter according to claim 5, wherein a thickness of the protruding portion at a position in contact with the main body portion is larger than a thickness of the protruding portion at a position in contact with the inner wall.

7. The filter according to claim 1, wherein the protruding portion has a surface continuous with the first main surface.

8. The filter according to claim 1, wherein the protruding portion has a surface recessed with respect to the first main surface.

9. The filter according to claim 3, wherein the protruding portion has a surface recessed with respect to the first main surface.

10. The filter according to claim 1, wherein the protruding portion seals a through-hole of the plurality of through-holes in which the fixing portion located on the sidewall side of the main body portion is arranged.

11. The filter according to claim 1,
  wherein the sidewall is a first sidewall, the protruding portion is a first protruding portion, and the fixing portion is a first fixing portion,
  the main body portion further includes a second sidewall facing the first sidewall, and
  the support portion further includes a second protruding portion protruding toward an outer side portion of the main body portion in a direction along the first main surface from a second fixing portion located on the second sidewall side of the main body portion among the plurality of fixing portions.

12. The filter according to claim 1, wherein a thermal expansion coefficient of a material of the filter base portion and a thermal expansion coefficient of a material of the support portion are substantially equal to each other.

13. The filter according to claim 1, wherein the support portion includes:
  a plurality of first support members having the main body portion and the protruding portion and extending in a first direction; and
  a plurality of second support members having the main body portion and the protruding portion and extending in a second direction intersecting the first direction.

* * * * *